United States Patent [19]

Kuzuya et al.

[11] Patent Number: 4,621,076

[45] Date of Patent: Nov. 4, 1986

[54] PHARMACEUTICAL COMPOSITION USEFUL FOR INHIBITING PLATELET AGGREGATION

[75] Inventors: Fumio Kuzuya; Kyoji Kito, both of Nagoya; Hisaaki Uchida, Kounan, all of Japan

[73] Assignee: Meito Sangyo Kabushiki Kaisha, Aichi, Japan

[21] Appl. No.: 702,424

[22] Filed: Feb. 15, 1985

Related U.S. Application Data

[63] Continuation of Ser. No. 543,942, Oct. 19, 1983, abandoned.

[30] Foreign Application Priority Data

Oct. 21, 1982 [JP] Japan .................. 57-183676

[51] Int. Cl.⁴ ............................................. A61K 31/70
[52] U.S. Cl. ....................................... 514/48; 514/822
[58] Field of Search ................................ 514/48, 822

[56] References Cited

PUBLICATIONS

Packham et al. Am. J. Physiol., vol. 227, No. 5 1974, pp. 1143–1148.

Maguire et al. Experientia, vol. 30, No. 8 1974, pp. 922–924.

Nikulin, A. A., Cited in Chem. Abstracts, vol. 89 1978, 3687c.

The Merck Index, 9th ed. 1976, p. 594, #4421, 4422.

*Primary Examiner*—Donald B. Moyer
*Assistant Examiner*—Jacqueline M. Stone
*Attorney, Agent, or Firm*—Wenderoth, Lind & Ponack

[57] ABSTRACT

A pharmaceutical composition comprising an amount, effective for inhibiting platelet aggregation, of quanosine monophosphate represented by the following formula

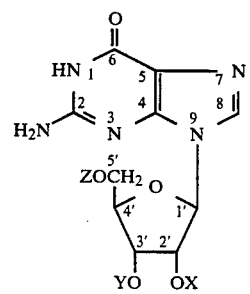

wherein one of X, Y and Z represents a $H_2PO_3$ group and the remaining two of these represent a hydrogen atom, or a pharmaceutically acceptable salt thereof and a pharmaceutically acceptable diluent or carrier.

2 Claims, No Drawings

PHARMACEUTICAL COMPOSITION USEFUL FOR INHIBITING PLATELET AGGREGATION

This application is a continuation of now abandoned application Ser. No. 543,942, filed Oct. 19, 1983.

This invention relates to a pharmaceutical composition useful for inhibiting platelet aggregation comprising guanosine monophosphate (GMP), a known compound, or its pharmaceutically acceptable salt as an active ingredient.

More specifically, this invention relates to a pharmaceutical composition comprising an amount, effective for inhibiting platelet aggregation, of guanosine monophosphate represented by the following formula (I)

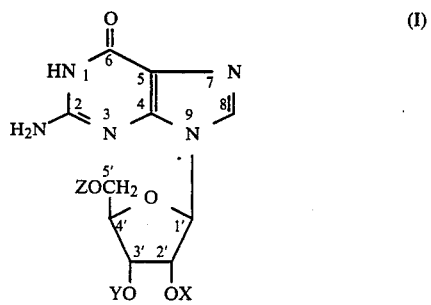

wherein one of X, Y and Z represents a $H_2PO_3$ group and the remaining two of these represent a hydrogen atom,
or a pharmaceutically acceptable salt thereof.

When damage is done to vessel walls owing to trauma, aterosclerosis or by other causes, endothelial cells desquamate to expose the collagen under the endothelium. Platelets stick to the exposed collagen and release various substances they posesses, such as adenosine 5'-diphosphate (to be referred to as 5'-ADP) and platelet factor 3. These substances further make the platelets in the blood current sticky so that the platelets adhere to each other to form platelet thrombi (white thrombi). Furthermore, the released platelet factor 3 promotes the activity of the intrinsic blood coagulation system to form a firm fibrin network on the platelet thrombi formed. Erythrocytes are captured in the platelet thrombi to form complete thrombi (red thrombi).

The thrombi so formed do not always stay at the site of formation, and may circulate in the blood current. Thrombi in such a state are called emboli, and may finally lodge in fine capillaries of the limbs, heart, cerebrum. If they block the blood current of the heart or cerebrum, they might cause myocardial infarction or cerebral ischemia.

As stated above, it is well known that platelets in the blood are an important factor in the formation of a thrombus. In view of this, many attempts have been made in the past to use drugs capable of inhibiting platelet aggregation for the prevention and treatment of thrombotic diseases.

Known antiplatelet drugs include non-steroidal anti-inflammatory agents such as aspirin and indomethacin, pyrazole derivatives such as sulfinpyrazone, and pyrimidopyrimidine derivatives such as dipyridamole. It has been desired to develop antiplatelet drugs which are better in pharmacological effect and safety than the conventional drugs exemplified above.

Anti-coagulants such as heparin and dicumarol which inhibit the activity of the intrinsic blood coagulation system have long been used as drugs for preventing and treating thrombotic diseases. Since, however, these drugs cause a bleeding tendency when administered in excess, it is necessary to measure the blood coagulation time regularly during the period of administration so that the dose of the drug may not become excessive. In actual use, therefore, such drugs have the disadvantage of being restricted in many ways.

On the other hand, platelet aggregation inhibitors which inhibit formation of platelet thrombi do not cause such undesirable phenomena as in the anticoagulants even when administered in excess, and are advantageous over the anticoagulants when used as drugs for treating thrombotic diseases.

It is known that some nucleoside phosphates affect such platelet aggregation. For example, it is known that adenosine 5'-diphosphate (5'-ADP) shows an action of promoting platelet aggregation, whereas adenosine 5'-monophosphate (5'-AMP) has a weak action of inhibiting platelet aggregation [M. H. Maguire et al., Experientia, 30, (8), 922–4 (1974)]. In an attempt to utilize such actions, various derivatives of adenosine have previously been synthesized, and it has been reported that some of them exhibit platelet aggregation inhibiting activity.

To the best of the knowledges of the present inventors, however, it has not yet been known that guanosine monophosphate (GMP) has platelet aggregation inhibiting activity.

It has previously been reported that at high concentrations, guanosine 5'-diphosphate (5'-GDP) has an inhibitory action on 5'-ADP-induced platelet aggregation (American Journal of Physiology, vol. 227, No. 5, pages 1143–1148, 1974).

This report, however, is quite silent on the action of guanosine monophosphate (GMP). Tests conducted by the present inventors show that 5'-GDP has no inhibitory action on thrombin-induced platelet aggregation. Furthermore, as stated above, it is known that 5'-ADP and 5'-AMP exhibit quite contrary actions on platelet aggregation.

The present inventors have made investigations on the effect of guanosine monophosphate (GMP) on platelet aggregation. These investigations have led to the discovery that the guanosine monophosphate represented by formula (I) exhibits strong platelet aggregation inhibiting activity, has very low toxicity, and can be used over a long period of time with accurate effects, and therefore, it is useful as an agent for treating thrombotic diseases.

Investigations of the present inventors have shown that the compound of formula (I) has a strong inhibitory action on thrombin-induced platelet aggregation, and in experiments on animals (rabbits) by oral and intravenous administrations and experiments on humans by oral administration, exhibits a strong inhibitory action on thrombin-induced platelet aggregation.

It is an object of this invention therefore to provide a pharmaceutical composition useful for inhibiting platelet aggregation comprising the known GMP of formula (I) or its pharmaceutically acceptable salt as an active ingredient.

The above and other objects and advantages of this invention will become apparent from the following description.

GMP of formula (I) is a known substance occurring in vivo. For example, it is present in the pancreas, liver, and spleen, and guanosine occurs in the spleen. These substances are said to perform a hormonic action, but no detail of their hormonic action has yet been known.

The compound of formula (I) can be produced by various known methods [see, for example, Methods in Carbohydrate Chemistry, VI, pages 451–456, Academic Press (1972); Y. Fujimoto and M. Teranishi, Selective Phosphorylation of Ribonucleosides].

One embodiment of its production will be described below. The starting guanosine [a compound of formula (I) in which all of X, Y and Z are hydrogen atoms] used in the production of the compound of formula (I) can be synthesized, for example, in the following manner.

The hydroxyl groups of ribose are protected with suitable protective groups such as acetyl or benzoyl groups by methods known per se. The reaction can be performed by the action of an acid anhydride such as acetic anhydride or an acid chloride such as benzoyl chloride using an organic base such as pyridine as a solvent. For example, the tetra-O-acetate (or benzoate) of ribose obtained as above is contacted with hydrogen bromide in a suitable solvent such as ether to form tri-O-acetyl(or benzoyl)-D-ribofuranosyl bromide, one reaction component. This reaction can be carried out, for example, by dissolving tetra-O-acetyl-beta-D-ribofuranose in ether saturated with hydrogen bromide gas at 0° C. and allowing the solution at 0° C. for 1 hour in a sealed condition.

On the other hand, by a method known per se, the 2-position of guanine is benzoylated and its 9-position is activated with mercuric chloride, thereby forming 2-benzoyl-9-chloromercury-guanine, the other reaction component. This reaction can be carried out, for example, by adding an ethanol solution of $HgCl_2$ to a mild alkali solution.

The two components which can be obtained as above are reacted in a suitable solvent such as dry xylene and the product is deprotected with an alkali to produce the starting guanosine. This reaction can be carried out, for example, by dissolving tri-O-acetyl-D-ribofuranosyl bromide in dry xylene, adding 2-benzoyl-9-chloromercury-guanine, and stirring the mixture under reflux for 2 hours in a moisture-free condition.

Guanosine 5'-monophosphate (5'-GMP), a compound of formula (I) in which X and Y are hydrogen atoms and Z is $H_2PO_3[P(O)(OH)_2]$, can be produced in the following manner from guanosine which can be obtained as above.

For example, the aforesaid guanosine is reacted with zinc chloride in acetone to introduce an isopropylidene group into the 2'- and 3'-hydroxyl groups of guanosine and reacting the product with 2-cyanoethylphosphoric acid in pyridine in the presence of dicyclohexyl carbodiimide (DCC) to cyanophosphorylate the 5'-position. The resulting compound is subjected to a deprotection reaction with lithium hydroxide and then a cation exchange resin (H+) to obtain 5'-GMP. This reaction can be carried out, for example, in the following manner. One mole of 2',3'-O-isopropylideneguanosine and 4 moles of 2-cyanoethylphosphoric acid are dissolved in 50% aqueous pyridine solution. The solvent is evaporated at 30° C. under reduced pressure. The residue is dissolved in pyridine and dicyclohexyl carbodiimide (DCC) is added, and the mixture is allowed to stand for 18 hours at room temperature. A small amount of water is added. The mixture is left to stand for 1 hour, and then concentrated under reduced pressure. A 0.4N aqueous solution of lithium hydroxide is added and the mixture is boiled under reflux for 1 hour.

Guanosine 3'-monophosphate (3'-GMP), a compound of formula (I) in which Y is $H_2PO_3$ and X and Z are hydrogen atoms, and guanosine 2'-monophosphate (2'-GMP), a compound of formula (I) in which X is $H_2PO_3$ and Z and Y are hydrogen atoms, can be obtained in the following manner in accordance with the method of Brown and Todd [D. M. Brown and A. R. Todd, J. Chem. Soc., 44 (1952)]. Specifically, guanosine and trityl chloride are reacted in anhydrous pyridine at 60° C. for 3 days to obtain 5'-tritylguanosine as a result of selective tritylation of the 5'-position. The resulting 5'-tritylguanosine is dissolved in pyridine, and while cooling the solution at −20° C., diphenylphosphoryl chloride was added to obtain a mixture of a trityl derivative of 2'-monophosphate of guanosine and 3'-monophosphate of guanosine. The mixture is dissolved in 80% acetic acid, and the solution is heated under reflux to remove the trityl group to obtain a mixture of 2'-GMP and 3'-GMP. The mixture is charged onto a column of Dowex 1 ® (formic acid type). The column is eluted with 0.1N formic acid to obtain guanosine 2'-monophosphate as an eluate, and with 1N formic acid to obtain guanosine 3'-monophosphate as an eluate. These eluates are each concentrated, lyophilized and recrystallized from water to separate the desired 2'-GMP and 3'-GMP.

The resulting compounds of formula (I) as an active ingredient in this invention may be in the form of their pharmaceutically acceptable salts. These salts can be obtained by adjusting the pH of an aqueous solution of GMP of formula (I) in free form to an acidic side with an inorganic or organic acid when an acid salt is desired, or to about 7.0 with an alkali hydroxide or aqueous ammonia when a basic salt is desired, and injecting the acidified or neutralized aqueous solution of GMP into ethanol.

Examples of the pharmaceutically acceptable salts of GMP of formula (I) which can be obtained as above include mineral acid salts such as sulfates, hydrochlorides and hydrobromides, alkali metal salts such as sodium and potassium salts, alkaline earth metal salts such as calcium and magnesium salts, aluminum salts, ammonium salts, organic acid salts such as benzoates, fumarates, succinates, tartrates and citrates and fatty acid salts such as stearates, palmitates and linolates.

Tests in vitro and in vivo were conducted for the inhibitory effect of guanosine 5'-monophosphate (5'-GMP) chosen as a typical example of the compound of formula (I) on platelet aggregation. The procedures and the results are shown below.

(1) Inhibitory effect of GMP on platelet aggregation induced by various platelet aggregation inducing substances:

The inhibitory effect was measured by the method of Born (J. Physiol., vol. 168, p. 178, 1963).

Blood was drawn from the cubital vein of a healthy person with a care taken to avoid congestion. One part by volume of a 3.8% sodium citrate solution was added to 9 parts by volume of the blood, and the mixture was centrifuged at 1,000 rpm for 10 minutes at room temperature to obtain platelet-rich plasma (PRP). 0.1 ml of a solution of 5'-GMP sodium salt in each of the concentrations shown in Table 1 below was added to 0.7 ml of PRP, and then each of the various platelet aggregation inducing agents shown in Table 1 was added. Changes in absorbance were measured by an aggregometer (made by Evans Company), and the rate of platelet aggregation inhibition was calculated from the following equation.

$$\text{Rate of platelet aggregation inhibition (\%)} = \frac{C - S}{C} \times 100$$

where C is a change in absorbance which shows the maximum rate of aggregation when physiological saline was added, and S is a change in absorbance which shows the maximum aggregation when the test substance was added.

The results are shown in Table 1.

TABLE 1

| Platelet aggregation inducing agent | Concentration of the sample (mg/ml) | Rate of inhibition (%) |
| --- | --- | --- |
| Arachidonic acid (55.5 γ/ml) | 0.01 | 22 |
| | 1.00 | 40 |
| Collagen (5.5 γ/ml) | 0.10 | 10 |
| | 1.00 | 10 |
| 5'-ADP (*) (55.5 γ/ml) | 0.10 | 3 |
| | 1.00 | 10 |
| Norepinephrine (55.5 γ/ml) | 1.00 | 8 |
| Thrombin (0.5 μ/ml) | 0.1 | 66 |
| | 1.0 | 80 |
| | 10.0 | 89 |

(*) 5'-ADP: adenosine 5'-diphosphate

It is seen from Table 1 that 5'-GMP shows an inhibitory effect on all of the aggregation inducing agents tested, but is especially effective against thrombin-induced aggregation.

(2) Inhibitory effect of the compound of general formula (I) on thrombin-induced platelet aggregation in vitro:

The same experiment as in (1) above was carried out except that 0.25 μ/ml of thrombin was used as a platelet aggregation inducing agent. The results are shown in Table 2.

TABLE 2

| Compound of formula (I) | Concentration of the compound of formula (I) (mg/ml) | Inhibition rate (%) |
| --- | --- | --- |
| 5'-GMP (sodium salt) | 0.5 | 75 |
| | 1.0 | 81 |
| 3'-GMP (sodium salt) | 2.0 | 87 |
| | 2.0 | 80 |

Table 2 shows that both of the compounds of formula (I) have a strong inhibitory effect against thrombin-induced platelet aggregation.

(3) Inhibitory effect on platelet aggregation in vivo:
(1) Duration of the aggregation inhibiting effect.

5'-GMP sodium salt was administered to rabbits intravenously in a dose of 50 mg/kg or orally in a dose of 1 g/kg. After a predetermined period of time (30 seconds to 4 minutes in the case of intravenous injection, and 1 to 5 hours in oral administration), blood was drawn from the animals. One part by volume of a 3.8% solution of sodium citrate was added to 9 parts by volume of the blood, and the mixture was centrifuged at 1,000 rpm at room temperature for 10 minutes to obtain platelet-rich plasma (PRP). 0.1 ml of a thrombin solution (0.75 u/ml) was added to 0.7 ml of PRP, and then changes in absorbance were measured by an aggregometer (made by Evans Company). The results are shown in Tables 3 and 4.

(i) Intravenous administration

TABLE 3

| Time elapsed (seconds) | 30 | 60 | 90 | 120 | 180 | 240 |
| --- | --- | --- | --- | --- | --- | --- |
| Rate of platelet aggregation inhibition (%) | 94 | 93 | 59 | 60 | 62 | 27 |

(ii) Oral administration

TABLE 4

| Time elapsed (hours) | 1 | 2 | 3 | 4 | 5 |
| --- | --- | --- | --- | --- | --- |
| Rate of platelet aggregation inhibition (%) | 95 | 95 | 93 | 93 | 83 |

It is seen from these tables that 5'-GMP shows a marked inhibition of platelet aggregation even in oral administration, and its effect lasted even after the lapse of 5 hours.

(2) Relation between the dose of GMP and the aggregation inhibiting effect.

Using rabbits, the dose response of the platelet aggregation inhibiting activity of 5'-GMP (sodium salt) in vivo was examined. 5'-GMP (sodium salt) was orally administered to the rabbits, and blood was drawn from the animals one hour after the administration. PRP was prepared in the same way as in section (1) above. The degree of platelet aggregation inhibition was measured by an aggregometer. The results are shown in Table 5.

TABLE 5

| Dose of GMP (g/kg) | 0.5 | 1.0 | 1.5 | 2.0 | 3.0 |
| --- | --- | --- | --- | --- | --- |
| Rate of platelet aggregation inhibition (%) | 38.8 | 61.0 | 75.2 | 80.3 | 100 |

(4) Inhibitory effect on platelet aggregation in humans in vivo:

One gram of 5'-GMP (sodium salt) was administered orally to each of five healthy persons, and blood was drawn from them after a predetermined period of time. One part by volume of a 3.8% aqueous solution of sodium citrate was added to 9 parts by volume of the blood, and the mixture was centrifuged at room temperature for 10 minutes at 1,000 rpm to obtain platelet-rich plasma (PRP). 0.1 ml of a thrombin solution (0.75 u/ml) was added to 0.7 ml of PRP, and changes in absorbance were measured by an aggregometer (made by Evans Company). The results are shown in Table 6.

It is seen from Table 6 that the effect of 5'-GMP was observed in humans even after the lapse of 4.5 hours from administration.

TABLE 6

| Time elapsed (hours) | 1.5 | 3 | 4.5 |
|---|---|---|---|
| Rate of platelet aggregation inhibition (%) | 63 | 75 | 62 |

(5) Acute toxicity:

The acute toxicity of the compound of formula (I) in accordance with this invention was examined.

The test compound (guanosine 5'-monophosphate sodium salt) was dissolved in physiological saline, and the solution was administered to ddY-strain mice (body weight 20 to 25 g) intravenously or orally. After the administration, the animals were observed for three days, and the $LD_{50}$ values of the test compound were calculated by the Litchfield-Wilcoxon method.

The results are shown in Table 7 below. The parenthesized figures show 95% reliability limits.

TABLE 7

| Compound | $LD_{50}$ (g/kg) |
|---|---|
| 5'-GMP (sodium salt) (iv) | 3.35 (2.96–3.79) |
| 5'-GMP (sodium salt) (po) | 14.8 (12.9–17.0) |

As shown by the foregoing pharmacological data and the results of the toxicity test above, the active ingredient used in this invention exhibits an excellent platelet aggregation inhibiting effect and has low toxicity. The pharmaceutical composition of this invention containing this active ingredient is useful as an agent for treating thrombotic diseases.

The active ingredient in accordance with this invention is characterized by showing an especially strong inhibitory activity on thrombin-induced platelet aggregation which is not seen in conventional platelet aggregation inhibitors, and, therefore, is expected to produce an effect not attainable by the conventional platelet aggregation inhibitors.

The pharmaceutical composition of this invention is useful for the prevention and treatment of cerebral vessel disorders such as cerebral ischemia and transient ischemic attack (TIA) by thrombosis and embolism in cerebral vessels, and thrombotic diseases typified by ischemic heart disease, peripheral arterial thrombosis, deep vein thrombosis and thrombotic thrombocytopenic purura. It can also be utilized for preventing formation of thrombi in an arteriovenous shunt or an arterial catheter during dialysis of blood and in artificial valves.

The pharmaceutical composition of this invention may be used as the guanosine monophosphate of formula (I) or it pharmaceutically acceptable salt alone or a mixture of such guanosine monophosphates or their salts. Usually, it can be used together with a pharmaceutically acceptable diluent or carrier in various dosage forms such as powders, granules, capsules, tablets, syrup, aqueous preparations, other orally administrable forms, and parenteral preparations such as injectable preparations.

Various liquid or solid diluents or carriers can be used for this purpose. Examples of the solid diluents or carriers include calcium phosphate, calcium carbonate, glucose, lactose, sucrose, dextrin, sucrose esters, starch, sorbitol, mannitol, crystalline cellulose, talc, kaolin, synthetic aluminum silicate, carboxymethyl cellulose, methyl cellulose, celluloce acetate phthalate, sodium alginate, polyvinyl pyrrolidone, polyvinyl alcohol, gum arabic tragacanth gum, gelatin, agar powder and shellac. Examples of the liquid diluents or carriers include water, physiological saline, ethanol, propylene glycol, polyethylene glycol, glycerol and Linger's solution.

The pharmaceutical composition of this invention comprises an amount, effective for inhibiting platelet aggregation, of GMP or its pharmaceutically acceptable salt. The amount can be selected properly, and for example, it is about 1 to about 99% by weight, preferably about 5 to about 90% by weight.

The effective dose of the compound of formula (I) varies depending upon the condition of the subject, the route of administration, etc. For example, in intravenous administration, it is about 50 to 0.01 mg/kg, preferably about 20 to 0.1 mg/kg, per day per adult. In the case of oral administration, it is about 500 to 1 mg/kg, preferably about 200 to 5 mg/kg, per day per adult.

The following Examples illustrate some embodiments of the present invention more specifically. It should be understood that these are merely illustrative, and various changes are possible within the disclosure and scope of the invention.

EXAMPLE 1

| Tablet:- | |
|---|---|
| 5'-GMP (sodium salt) | 50 g |
| Lactose | 90 g |
| Corn starch | 35 g |
| Hydroxypropyl cellulose | 5 g |
| Calcium stearate | 2 g |
| | 182 g |

The above ingredients were mixed and compressed by a tableting machine to form tablets each containing the indicated amounts of the above ingredients.

Tablets were prepared in the same way as above except that a potassium or magnesium salt of 5'-GMP was used instead of 5'-GMP sodium salt.

EXAMPLE 2

| 2'-GMP (sodium salt) | 50 g |
|---|---|
| Lactose | 60 g |
| Potato starch | 50 g |
| Crystalline cellulose | 10 g |
| Calcium stearate | 1 g |
| | 171 g |

The above ingredients were filled in capsules to form capsules each containing 100 mg of the active ingredient.

Capsules were similarly prepared by using a calcium or aluminum salt of 2'-GMP instead of 2'-GMP.

EXAMPLE 3

| Injectable preparation:- | |
|---|---|
| 3'-GMP (sodium salt) | 25 g |
| D-sorbitol | 20 g |
| Distilled water for injection | 500 ml |

A solution composed of the above ingredients was filtered by a membrane filter (0.22 μm), and dividedly filled into 2 ml. ampoules. The ampoules were meltsealed, and then heat-sterilized in a customary manner to form injectable preparations.

Example 4

| Granules:- | |
|---|---|
| 5'-GMP (sodium salt) | 100 g |
| Lactose | 28 g |
| Hydroxypropyl cellulose | 2 g |
| | 130 g |

The above ingredients were weighed. First, 5'-GMP (sodium salt) and lactose were uniformly mixed. Then, hydroxypropyl cellulose was dissolved in isopropanol, and the solution was added to the aforesaid mixture of the two ingredients. The mixture was granulated by a wet granulating method to form granules.

Granules were similarly obtained by repeating the above procedure except that an ammonium or stearic acid salt of 5'-GMP was used instead of 5'-GMP sodium salt.

EXAMPLE 5

| Powder:- | |
|---|---|
| 5'-GMP | 30 g |
| Lactose | 40 g |
| Starch | 27 g |
| Colloidal silica | g |
| | 100 g |

The above ingredients were processed in a customary manner to form a powder.

A powder was prepared in the same way as above except that 3'-GMP was used instead of 5'-GMP.

EXAMPLE 6

| Trouche:- | |
|---|---|
| 5'-GMP sodium salt | 15.0 g |
| Glucose | 66.7 g |
| Dipotassium phosphate | 0.2 g |
| Monopotassium phosphate | 0.1 g |
| Flavor | 1.0 g |
| Lactose | 17.0 g |
| Magnesium stearate | suitable amount |
| | 100 g |

A trouch was prepared in a customary manner from the above ingredients.

What is claimed is:

1. A method for inhibiting blood platelet aggregation which comprises orally adminstering to a human patient, suffering from cerebral ischemia or transient ischemic attack by thrombosis or embolism in cerebral vessels, a platelet aggregation inhibiting amount of guanosine 5'-monophosphate represented by the formula

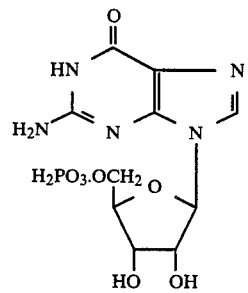

or a pharmaceutically acceptable salt thereof.

2. A method as recited in claim 1, wherein the dose of the guanosine 5'-monophosphate of said formula or its salt in the oral administration is about 500 to 1 mg/kg per day.

* * * * *